United States Patent
Rick et al.

(10) Patent No.: US 9,772,389 B2
(45) Date of Patent: Sep. 26, 2017

(54) METHOD AND MAGNETIC RESONANCE APPARATUS FOR IMAGE ACQUISITION CONTROL WITH ADMINISTRATION OF CONTRAST AGENT

(71) Applicant: Siemens Aktiengesellschaft, Munich (DE)

(72) Inventors: Manuela Rick, Buckenhof (DE); Peter Schmitt, Weisendorf (DE); Andre de Oliveira, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 473 days.

(21) Appl. No.: 14/301,588

(22) Filed: Jun. 11, 2014

(65) Prior Publication Data
US 2014/0364724 A1 Dec. 11, 2014

(30) Foreign Application Priority Data
Jun. 11, 2013 (DE) .................. 10 2013 210 879

(51) Int. Cl.
*G01R 33/56* (2006.01)
*A61B 5/055* (2006.01)
*A61B 5/026* (2006.01)

(52) U.S. Cl.
CPC ........ *G01R 33/5601* (2013.01); *A61B 5/0263* (2013.01); *A61B 5/055* (2013.01)

(58) Field of Classification Search
CPC .... G01R 33/5601; A61B 5/0263; A61B 5/055
USPC ....................................................... 600/420
See application file for complete search history.

(56) References Cited

U.S. PATENT DOCUMENTS

| 2003/0036694 A1* | 2/2003 | Liu ................. | G01R 33/563 600/413 |
| 2007/0238956 A1* | 10/2007 | Haras .............. | A61B 6/032 600/407 |
| 2008/0306381 A1* | 12/2008 | Feuerlein ......... | A61B 6/032 600/425 |

FOREIGN PATENT DOCUMENTS

NO   WO 2012070951 A1 *  5/2012   ............. A61B 5/055

OTHER PUBLICATIONS

"Optimization of Contrast Timing for Breath-Hold Three-Dimensional MR Angiography," Hany et al., Journal of Magnetic Resonance Imaging, vol. 7 (1997), pp. 551-556.

(Continued)

*Primary Examiner* — Katherine Fernandez
*Assistant Examiner* — Katherine McDonald
(74) *Attorney, Agent, or Firm* — Schiff Hardin LLP

(57) ABSTRACT

In a method and magnetic resonance apparatus to acquire diagnostic image data of a contrast agent-filled target area of a patient, a peak time of the test bolus in the target area is automatically determined, from which a wait period is then determined for administering the main bolus. After the main bolus has been administered to the patient, magnetic resonance images of the target area are acquired, and each is analyzed immediately after acquisition thereof to determine whether that image shows arrival of the contrast agent. If and when one of these images shows such arrival, an acquisition protocol is immediately started in order to acquire the diagnostic image data set. If none of these images shows arrival of the contrast agent, the protocol to acquire diagnostic image data is started after the wait period.

14 Claims, 2 Drawing Sheets

(56) References Cited

OTHER PUBLICATIONS

"Automatic Bolus Detection in Breast MRI: a method to improve accuracy and reliability?," Geppert et al., Proc. Intl. Soc. Mag. Reson. Med., vol. 19 (2011), p. 3085.

* cited by examiner

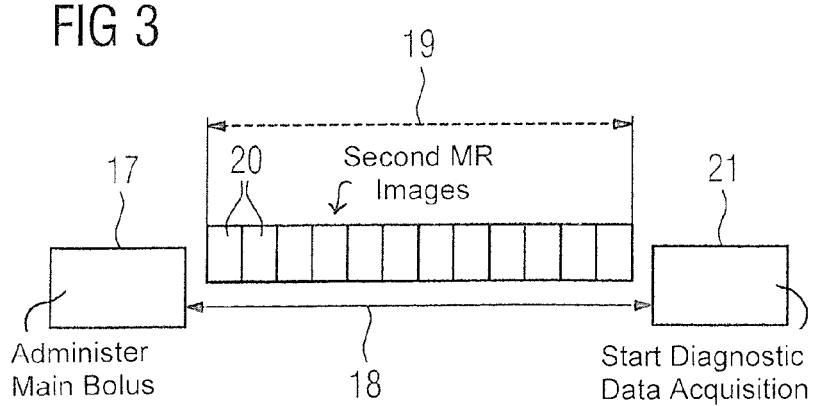
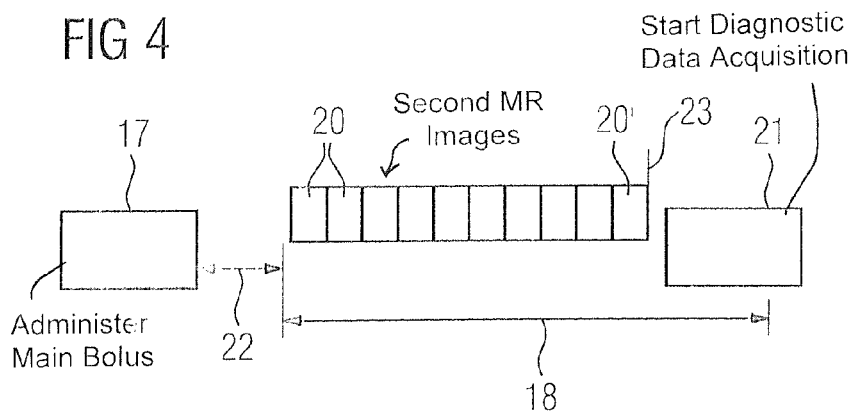
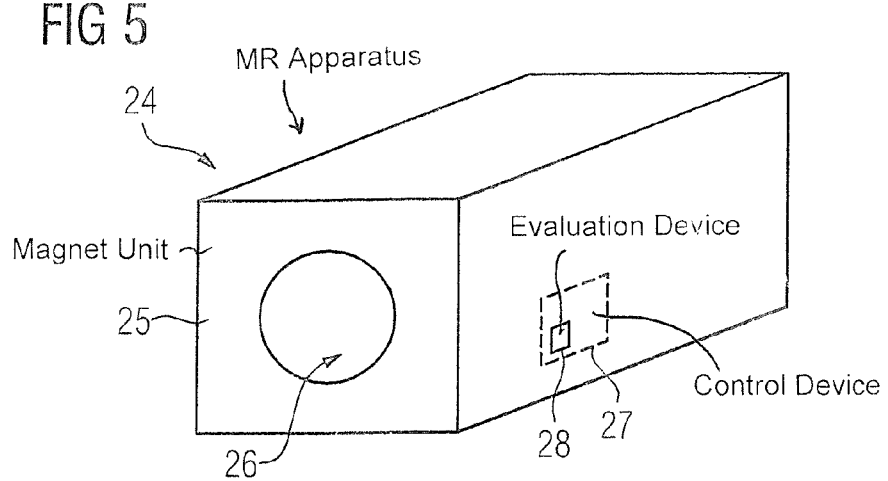

METHOD AND MAGNETIC RESONANCE APPARATUS FOR IMAGE ACQUISITION CONTROL WITH ADMINISTRATION OF CONTRAST AGENT

BACKGROUND OF THE INVENTION

Field of the Invention

The present invention concerns a method to control the acquisition of a diagnostic image data set of at least one part of a contrast agent-filled target area of a patient with a magnetic resonance device according to an acquisition protocol, as well as a magnetic resonance apparatus designed to perform such a method.

Description of the Prior Art

Contrast agent is often used within the scope of magnetic resonance imaging, in particular when image exposures should be produced within the context of dynamic processes, and for perfusion data acquisition in the vascular system of a patient. One important sign of quality of the image data sets that are acquired in this manner is that a good contrast agent filling is present. This means that the acquisition of the image data set must be implemented so that the acquisition region is optimally filled with contrast agent during the entire acquisition time. Magnetic resonance imaging thereby differs from other imaging modalities (for example computed tomography) because it is often a goal that data to be entered into the center of k-space are to be acquired at the point in time of the greatest contrast agent concentration in the acquisition region, since in this way the contrast-to-noise ratio (CNR) can be maximized. In other words: it is thus the goal to be able to cause the peak of the contrast agent concentration in the arterial or venous phase (depending on the acquisition goal) to occur simultaneously with the acquisition of the k-space center data.

In order to achieve this, it is known to use the test bolus technique within the scope of magnetic resonance angiography. In this technique, first bolus of the contrast agent (the test bolus) is initially injected that has a smaller amount of contrast agent than the main bolus to be administered for the diagnostic image acquisition, while first magnetic resonance images are acquired using a suitable magnetic resonance sequence in a first acquisition area that ideally corresponds to the acquisition area of the diagnostic image data set that is to be acquired later. These first magnetic resonance images can then be evaluated in order to determine the time from the administration of the test bolus to the time of highest contrast agent concentration in the acquisition area of the image data set (designated as peak time in the following). It is thus ultimately determined how long the test bolus requires in order to arrive in the acquisition area of the diagnostic image data set, and thus when the ideal point in time exists for acquisition of the k-space center.

After the test bolus measurement, the actual clinical examination is conducted. After the administration of the main bolus of the contrast agent, the acquisition protocol for the image data set is started only after a wait period that results from the peak time determined in the test bolus measurement. For example, such a procedure is described in an article by Thomas F. Hany et al., "Optimization of Contrast Timing for Breath-Hold Three-dimensional MR Angiography", JMRI 1997; 7:551-556.

However, a number of problems occur in a test bolus measurement. It is possible that, due to a human error, the contrast agent is administered too early, for example, by a start signal for the wait period being provided with a time offset toward the injection of the contrast agent of the main bolus. This problem exists because the synchronization between the injection of the contrast agent and the start of the wait period must occur manually on the part of the user because, although contrast agent injectors that can automatically trigger the start of a wait period are known in computed tomography systems, an automatic injection controller for magnetic resonance systems is not yet known because it is extremely complicated to produce magnetic resonance-compatible devices. If the contrast agent is administered too early—meaning before the beginning of the wait period—this has the result that the acquisition protocol (and thus the measurement of the image data set) begins too late, such that the image data set overall has a poorer quality, in particular because venous portions can already be present in the arterial imaging and the like. In the worst case, the examination must be shifted to a further day because the amount of contrast agent that can be administered to a patient within a given time duration is limited.

An additional problem is the possibility of a variation of the physiological situation of the patient. For example, if the patient is excited, adrenalin can be produced, which increases the circulation speed so that it may occur, due to such physiological causes, that the contrast agent arrives before the wait period has ended, such that a non-optimal image data set is acquired.

Other variants in order to start the acquisition protocol for the image data set optimally at the correct point in time are likewise known in the prior art. Naturally it is possible to manually detect the main bolus. Magnetic resonance images of a second acquisition area (which is often selected at a certain distance from the acquisition area of the diagnostic image data set) can be acquired that have a high temporal resolution. For example, such magnetic resonance images can show a blood vessel that will feed the main bolus to the actual acquisition area of interest. When the arrival of the contrast agent is detected in the magnetic resonance images, the start of the acquisition protocol is triggered manually.

A further variation of this procedure is the automatic tracking of the main bolus (bolus tracking, also known under the keyword "care bolus"). Because the full dose of the contrast agent was injected as the main bolus, the arrival of the contrast agent in the second acquisition area is hereby automatically detected by a post-processing and evaluation of the magnetic resonance image that starts immediately after acquisition of a magnetic resonance image of the second acquisition area. The acquisition protocol is started automatically after the automatic detection of the contrast agent. For example, such a method is described in an article by C. Geppert et al., "Automatic Bolus Detection in Breast MRI: a method to improve accuracy and reliability?", Proc. Intl. Soc. Mag. Reson. Med. 19 (2011), 3085.

Such procedures for automatic bolus detection ("care bolus") also have disadvantages. A first intrinsic problem of this variant is the selection of the second acquisition area, which does not correspond to the acquisition area of the image data set (and naturally also does not correspond to the first acquisition area in a test bolus measurement). This is due to the fact that some time is required in order to execute the start of the actual imaging, (acquisition protocols often include speech commands), and the time until the k-space center is measured can necessarily also be in the range of seconds. The estimation of a suitable second acquisition area is extremely difficult, and as a consequence a further problem of automatic bolus detection results from the poor time resolution of this method because, for example, data of new magnetic resonance images are present only every second or every two seconds. This poor time resolution, and the fact that the time that the blood (and thus the contrast agent bolus) requires in order to arrive from the second acquisition area to the acquisition area of the image data set is very short, have the result that compromises are often necessary in the quality of the image data sets. In this context, it is also known to use extremely short speech commands.

SUMMARY OF THE INVENTION

An object of the present invention is to provide a method to control the image acquisition operation in a measurement with contrast agent that enables an increase in the image quality while avoiding the disadvantages of the cited methods of the prior art.

This object is achieved by a method having the following steps according to the invention.
- after administration of a test bolus that includes less contrast agent than a subsequent main bolus to be administered to acquire the image data set, with the magnetic resonance device acquire first magnetic resonance images of the first acquisition area including at least a portion of the target area,
- evaluate the first magnetic resonance images to determine a peak time of the test bolus in the target area, which peak time describes a point in time of maximum concentration,
- using the peak time, determine a wait period after administration of the main bolus,
- after administration of the main bolus, acquire in chronological succession multiple second magnetic resonance images of a second acquisition area including at least a portion of the target area in a monitoring interval situated within the wait period,
- immediately after acquisition of one of the second magnetic resonance images, evaluate the just acquired second magnetic resonance image to determine a possible arrival of the main bolus in the target area,
- given determination from a second magnetic resonance image of an arrival of the main bolus in the target area, terminate the acquisition of the second magnetic resonance images and immediately start the acquisition protocol to acquire the image data set,
- in the event that no arrival of the main bolus is determined in a second magnetic resonance image, start the acquisition protocol to acquire the image data set after the wait period.

The basis of the present invention is thus to ultimately combine the test bolus method and automatic detection of the main bolus (bolus tracking) in order to achieve the advantages of both measurement methods. For this purpose, the wait period between the injection of the main bolus and the start of the acquisition protocol (which is present in the test bolus method) is filled with measurements (data acquisitions) of second magnetic resonance images that have a high temporal resolution. As in a procedure with automatic detection of the main bolus, in these second magnetic resonance images it can ultimately be checked whether an early administration of the contrast agent has taken place. Because the wait period would be present anyway, there are no disadvantages to filling these with the measurements of the second magnetic resonance images. The primary advantage of the procedure according to the invention results from this: that the robustness of the test bolus method is increased because a start of the measurement that is markedly too late is avoided without disadvantages being creating in the procedure. In addition, costs are reduced because measurements must be repeated in fewer patients. A high image quality is thereby maintained that can very exactly indicate the peak time at which the highest concentration of contrast agent is present in the acquisition area of the image data set, such that the start point in time of the acquisition protocol can be selected correctly in order to acquire the center of k-space at this time. If a time offset occurs once between the injection of the contrast agent and the beginning of the correspondingly determined wait period, a monitoring is implemented that ensures that the deviation is not too great, and consequently the image quality is increased even given such deviations, in particular because venous contaminations of arterial image data sets can be avoided, even if the peak time and the measurement time of the k-space center do not exactly coincide given a detection of the main bolus in the second magnetic resonance images.

At this point it is emphasized again that the administration of the contrast agent itself is not a part of the method according to the invention because the basis of the present invention is to combine the measurement method of the test bolus and the bolus tracking (which takes place via a control device of the magnetic resonance device, for example). In contrast to this, the administration of contrast agent is most often conducted manually at an external contrast agent injector.

Overall, an improvement is thus provided both with regard to the purely automatic bolus tracking and with regard to a pure test bolus method. In most cases according to conventional procedures, the precise test bolus measurement is based on the start of the acquisition protocol in which too early an arrival of the contrast agent in the acquisition area of the image data set occurs (be it due to an operator error or due to a physiological variation in the patient), thus resulting in a start of the acquisition protocol that is also too early. This is avoided in the inventive procedure. The dependency of the test bolus measurement on the physiological parameters of the patient is thus likewise reduced.

In a further embodiment of the present invention, the end of the monitoring interval is selected so that the time period from the end of the monitoring interval until the end of the wait period is shorter than or identical to the acquisition time for a second magnetic resonance image. In this way it can be ensured that the acquisition of the second magnetic resonance images does not affect the coincidence of the k-space center and the peak of the main bolus, such that in each case the acquisition protocol for acquisition of the image data set can be started at the correct point in time after the wait period.

The wait period can appropriately be calculated as the peak time minus a time until the measurement of the k-space center after the start of the acquisition protocol. In this way, the measurement of the k-space center occurs at the peak time, thus at the ideal point in time for improvement of the contrast/noise ratio. It is noted that the occurrence of a speech command to the patient can be provided at the beginning of the acquisition protocol, which speech command can thus be understood as belonging to the acquisition protocol according to the invention. When the time until the measurement of the k-space center from the beginning of the measurement process in the acquisition protocol is designated as ttc, and the time for the speech command (voice command) to the patient is designated as $t_{vc}$ the wait period $t_w$ depends on the peak time $t_b$ according to $$t_w = t_b - tcc - t_{vc}.$$

For the length of the monitoring interval, ideally the acquisition time of a second magnetic resonance image with the magnetic resonance sequence ($t_a$) is subtracted from the wait period $t_w$.

The peak time, can be determined from a temporal contrast agent progression curve determined from the first magnetic resonance images. For example, this curve can describe the amount of contrast agent in the first acquisition area (which ideally corresponds to the acquisition area of the image data set), such that the peak time can be determined by determining a maximum in the contrast agent progression curve. The contrast agent progression curve can thereby be generated via histogram calculation or digitization of the first magnetic resonance images, wherein more precise techniques are known in the prior art and do not need to be presented in detail here. It can be appropriate for the contrast agent curve to consider only the actual acquisition area of the image data set.

In a further embodiment of the invention it can be provided that the first acquisition area includes a boundary at the entrance side with regard to the contrast agent flow. This means that an edge of the target area can be appropriately considered at which the contrast agent bolus (here the main bolus) is first expected in order to thus achieve an optimally long reaction time at the start of the acquisition protocol.

As already noted, it is also advantageous if the first acquisition area corresponds to the acquisition area of the image data set. The point in time of maximum contrast agent concentration—thus the peak time—is then determined immediately for the correct area, such that fewer additional calculations and assumptions are required. Moreover, it is also conceivable to select the first acquisition area so that it includes the acquisition area of the image data set (its surroundings are consequently also observed), wherein a consideration to determine the peak time can be limited to the acquisition area of the image data set that is included in the first acquisition area, for example. However, in the first magnetic resonance images it can also be appropriate to also observe an edge or an additional flow path of the contrast agent towards the acquisition area of the image data set simultaneously with the acquisition area of the image data set.

In a further embodiment of the present invention, the second acquisition area is determined under consideration of image data of the first magnetic resonance images. This means that, in the first magnetic resonance images, the test bolus is observed over a longer time period and/or distance, such that a suitable position and/or orientation (thus attitude) of the second acquisition area can be determined in the target area in order to detect the arrival of the contrast agent as early as possible and—in the event that this occurs before the expiration of the wait period—to be able to start the acquisition protocol for the image data set correspondingly early. A synergy effect is thus used that is achieved via the use of both methods, thus the test bolus measurement and automatic bolus tracking.

A magnetic resonance sequence can be used for the acquisition of the second magnetic resonance images (which are in particular to be acquired as two-dimensional slices), which magnetic resonance sequence has an acquisition duration per second magnetic resonance image of less than two seconds, in particular less than one second, and/or the length of the monitoring interval can be selected so that at least five second magnetic resonance images (in particular at least 10 second magnetic resonance images) can be acquired in said monitoring interval. For the acquisition of the second magnetic resonance images, a magnetic resonance sequence with high temporal resolution is thus used that enables an optimally fast determination of an arrival of the main bolus in the target area. Suitable sequences are widely known in the prior art, wherein it is noted that ultimately the same basic sequence can be used for the acquisition of the first magnetic resonance images, the second magnetic resonance images and the image data set, wherein such a basic sequence is typically optimized for contrast agent measurements and can be parameterized in order to achieve a higher temporal resolution (for the first and second magnetic resonance images) or a higher spatial resolution (measurement of the image data set).

In addition to the method, the invention also concerns a magnetic resonance apparatus that has a control device designed to implement the method according to the invention. All statements with regard to the method according to the invention apply analogously to the magnetic resonance device according to the invention so that the cited advantages can also be achieved with the apparatus. In particular, the control device controls the other components of the magnetic resonance device at the corresponding points in time to acquire the first magnetic resonance images, the second magnetic resonance images and the image data set according to the acquisition protocol. The apparatus can additionally include an evaluation unit in which the peak time, the wait period and the length of the monitoring interval can be precisely determined with an evaluation of the second magnetic resonance images can taking place to determine an arrival of the main bolus in the target area.

BRIEF DESCRIPTION OF THE DRAWINGS

FIG. 3 is a flowchart for data acquisition in the method according to the invention.

FIG. 4 is a flowchart for data acquisition corresponding to FIG. 1, but with the use of the method according to the invention.

FIG. 5 schematically illustrates a magnetic resonance device according to the invention.

DESCRIPTION OF THE PREFERRED EMBODIMENTS

Figure 1:
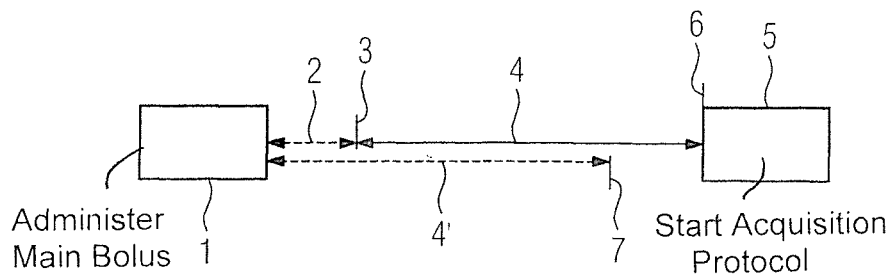
FIG. 1 is a flowchart for the administration of contrast agent in a test bolus measurement according to the prior art.

FIG. 1 explains a problem underlying the present invention in an example of a test bolus measurement according to the prior art. This involves the acquisition of an image data set with a magnetic resonance device, wherein it is thereupon sought that the k-space center coincides in agreement with a peak time in which the concentration of the contrast agent in the acquisition area of the image data set is highest. A smaller amount of contrast agent—what is known as the test bolus—is consequently administered in the test bolus method (as it is known from the prior art) than in the main bolus. First magnetic resonance images from which the peak time can be determined are acquired using a magnetic resonance sequence of high temporal resolution. With these images, a wait period is calculated for the main bolus with the measurement of the k-space center in that the time from the start of the acquisition protocol for the image data set up to the measurement of the k-space center is subtracted from the peak time which was measured as of the administration of the bolus. The wait period before the acquisition protocol is started should now extend after the administration of the main bolus.

However, the administration of the contrast agent for the main bolus and the start of the wait period are synchronized manually due to the difficulty of achieving magnetic resonance-compatible contrast agent injector devices; displacements can occur, which is explained in detail via FIG. 1. There the administration of the main bolus is identified with a box 1. If a delay period 2 now exists between the administration of the main bolus and the start point in time 3 at which the wait period 4 begins, the acquisition protocol indicated by the box 5 is only started at a point in time that is too late. The correct point in time 7 would be that at which the wait period 4' (measured from the administration of the main bolus, box 1) has elapsed. This has the consequence that the image data set acquired with the acquisition protocol is of poorer quality, wherein contaminations due to the venous phase can also occur given arterial acquisitions, for example.

A similar problem results if physiological parameters of the patient vary, for example if he is excited and the circulation speed increases. The determined wait period 4, 4' is then completely inapplicable since it is too long; this applies even if the administration of the main bolus and the start of the wait period take place synchronously (see wait period 4' in FIG. 1).

Figure 2:
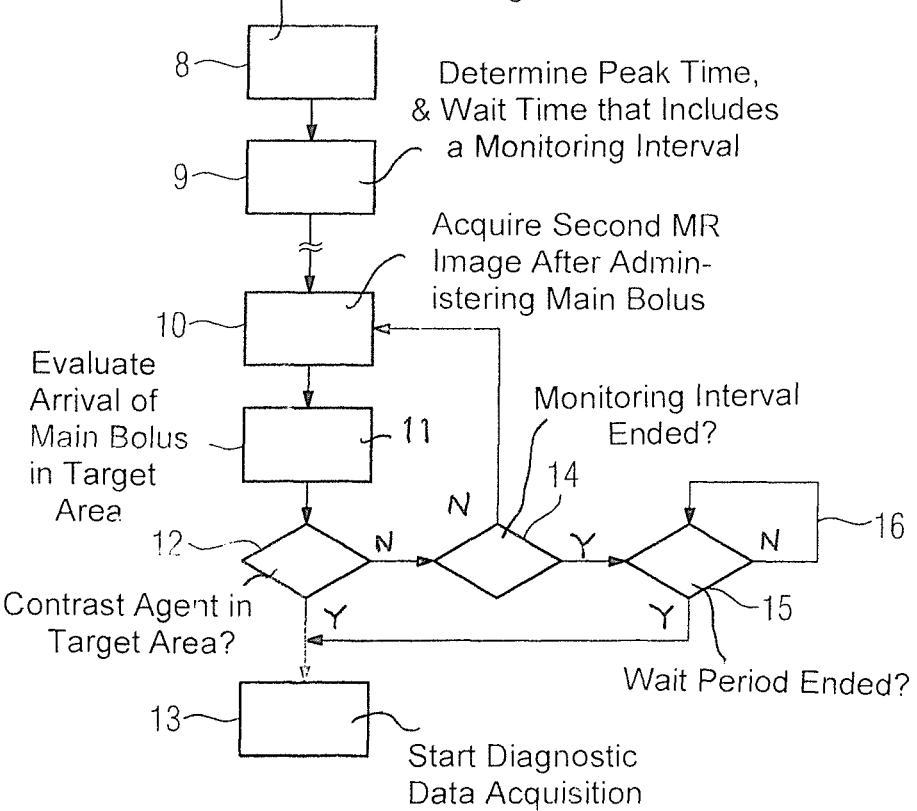
FIG. 2 is a flowchart of the method according to the invention.

Such quality losses can be avoided using the method according to the invention (which also entails additional advantages that have already been explained), as described in the following. An exemplary embodiment of the method according to the invention is shown as a flowchart in FIG. 2, which combines the variants of the test bolus measurement that are already fundamentally known in the prior art and the automatic bolus tracking.

After administration of a test bolus (which is not part of the method according to the invention), in Step 8 first magnetic resonance images of a first acquisition area in the target area are acquired over a time period covering at least the first passage of the target area. The first acquisition area is selected so that it corresponds to the acquisition area for the image data set, or includes this area. A magnetic resonance sequence that is optimized for the contrast agent imaging is used that is parameterized so that a high temporal resolution (for example of one second or less) is achieved. The result of Step 8 is thus a set of first magnetic resonance images that are evaluated in Step 9 in order to determine the peak time, the wait time and the duration of a monitoring interval. At present a contrast agent progression curve serves for this that describes the amount of contrast agent relative to the time in the acquisition area of the image data set, as this is basically known in the prior art. Here the maximum that corresponds to the peak time can easily be located.

If the peak time is known first, the wait period that is required so that the measurement of the k-space center and the maximum contrast agent concentration in the target area of the image data set coincide under the same conditions can be determined from this and from the knowledge of the acquisition protocol. An acquisition protocol for the image data set is thereby presently considered which includes a speech command (for example a breath hold command) which takes a time $t_{vc}$. The actual measurement begins after this, wherein the k-space center is read out after a time ttc. This thus means that the wait period can be determined as $$t_w = t_b - ttc - t_{vc},$$

wherein $t_b$ is the peak time.

Because the wait time $t_w$ should be used in the method according to the invention in order to monitor a possible early arrival of the main bolus, as will be explained in more detail in the following second magnetic resonance images are acquired in a monitoring interval (here with a magnetic resonance sequence that is similarly parameterized for good time resolution and optimized for contrast agent imaging), for example such that an acquisition time of one second per second magnetic resonance image results. This acquisition time for a second magnetic resonance image is designated with $t_a$, wherein the monitoring interval is defined in terms of its length so that the acquisition of the second magnetic resonance images cannot delay the start of the acquisition protocol, concretely present as $$t_m = t_w - t_a;$$

wherein $t_m$ indicates the length of the monitoring interval.

The acquisition and evaluation of the first magnetic resonance images in Steps 8 and 9 can thereby take place completely automatically via the control device of a magnetic resonance device; a start trigger is only necessary that coincides with the administration of the test bolus (which does not belong with the method according to the invention).

The second segment of the method according to the invention begins after the main bolus has been administered, which likewise does not belong with the method according to the invention. The passage of the wait period starts via a trigger, simultaneously with the administration of the main bolus, after which start the monitoring interval begins, which means that a second magnetic resonance image is acquired (Step 10). This shows a second acquisition region of the target area, but rather is a border region of the target area in which the main bolus will enter first so that is noticed as early as possible. It is noted that the first acquisition region of the first magnetic resonance images has presently been chosen to be larger so that, via its evaluation, parameters can be derived from the image data of the first magnetic resonance images, which parameters can be taken into account in the definition of the second acquisition region.

Immediately after the second magnetic resonance image has been acquired, in Step 11 it is evaluated as to whether the main bolus has already reached the target area (represented here by the second acquisition area). How the method proceeds further in Step 12 is dependent on the result of this evaluation. If it is established that contrast agent has already penetrated into the target area (for example too early an administration of the main bolus has consequently taken place, or physiological parameters of the patient have changed), in Step 13 the acquisition protocol for the image data set is started immediately after the acquisition of the second magnetic resonance images has been terminated.

However, if no contrast agent is visible in the second magnetic resonance image (which should be the more common case), the workflow proceeds with Step 14. In this a check is made as to whether the monitoring interval has already ended. If this is not the case, in Step 10 an additional second magnetic resonance image is acquired.

However, if the monitoring interval has expired, in Step 15 the workflow waits until the wait period has also ended, which is symbolized by the case 16. After the end of the wait period, in Step 13 the acquisition protocol is then started for the image data set.

This is now explained again in detail via the flowcharts in FIGS. 3 and 4. A box 17 again symbolizes the administration of the contrast agent of the main bolus (which is not a part of the invention). FIG. 3 shows a normal case in which the administration of the main bolus and the triggering of the beginning of the wait period 18 coincide. The monitoring interval 19, whose individual blocks 20 respectively symbolize the acquisition of a second magnetic resonance image, lies within the wait period 18. In this case, an early arrival of contrast agent in the second acquisition region is established in none of the second magnetic resonance images; this means that the physiological parameters of the patient have not significantly changed, such that the acquisition protocol can be started (block 21) after the expiration of the wait period 18.

FIG. 4 shows a case in which the trigger signal to start the wait period 18 was only provided after a delay period 22, which means that it was provided far too late. Accordingly, in the second magnetic resonance image of the block 20' an early contrast agent entrance into the target region is established in Step 11, such that the acquisition of the second magnetic resonance images is terminated at a point in time 23 in order to start the acquisition protocol late (Block 21). This means that the acquisition protocol is started directly after detection of contrast agent in the second magnetic resonance image, not right after the expiration of the wait period 18 (which would clearly only pass much too late). A delay of the start of the acquisition protocol is thus at least kept within limits.

FIG. 5 shows a block diagram of a magnetic resonance apparatus 24 according to the invention. As is basically known, apparatus 24 has a basic magnet unit 25 (commonly called a scanner) that surrounds a patient receptacle 26 into which a patient can be moved by a patient bed (not shown in detail here) in order to acquire magnetic resonance image data from the patient. Surrounding the patient receptacle 26 are typically a radio-frequency coil arrangement and a gradient coil arrangement. These components, like additional components of the magnetic resonance apparatus 24, are basically known in the prior art.

The magnetic resonance device 24 also has a control device 27 that is designed to implement the method according to the invention (consequently can control the remaining components of the magnetic resonance device 24 to acquire the first magnetic resonance images, the second magnetic resonance images and the image data set), and has an evaluation device 28 to implement Steps 9 and 11.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to control acquisition of a diagnostic magnetic resonance image data set from at least a portion of a contrast agent-filled target area of a patient, comprising:

after administering a test bolus of a contrast agent to the patient, said test bolus including less contrast agent than a subsequent main bolus to be administered to the patient to acquire the diagnostic magnetic resonance image data set, operating a magnetic resonance data acquisition scanner, adapted to receive the patient therein, to start and execute a magnetic resonance image data acquisition protocol in order to acquire first magnetic resonance images of a first acquisition area, which includes at least the portion of the target area to be acquired in said diagnostic magnetic resonance image data set;

providing said first magnetic resonance images to a computerized processor and, in said processor, automatically evaluating the first magnetic resonance images to determine a peak time of said test bolus in said target area, said peak time being a point in time of maximum concentration of said contrast agent in said target area;

in a diagnostic magnetic resonance image data acquisition protocol, acquiring said diagnostic magnetic resonance image data from the patient, and entering the diagnostic magnetic resonance image data into a memory organized as k-space having a k-space center into which said diagnostic magnetic resonance image data are entered at a time beginning after starting said diagnostic magnetic resonance image data acquisition protocol and, in said processor, calculating a wait period, which follows administration of said main bolus, as said peak time minus a duration until said entry of said diagnostic magnetic resonance image data into said k-space center begins after starting said magnetic resonance image data acquisition protocol;

after administering said main bolus to the patient, operating said magnetic resonance data acquisition scanner to acquire, in chronological succession, a plurality of second magnetic resonance images of a second acquisition area of the patient, which includes at least a portion of the target area, in a monitoring interval that is situated within said wait period;

successively providing said second magnetic resonance images to said processor immediately upon individual acquisition thereof and, in said processor, successively analyzing said second magnetic resonance images, as said second magnetic resonance images are supplied to said processor, to identify one of said second magnetic resonance images that shows arrival of said main bolus in said target area;

upon identifying said one of said second magnetic resonance images that shows arrival of said main bolus in said target area, providing a signal from said processor to said magnetic resonance data acquisition scanner that terminates acquisition of said second magnetic resonance images and that immediately starts said diagnostic magnetic resonance image data acquisition protocol, wherein said magnetic resonance data acquisition scanner is operated by the processor to acquire said diagnostic magnetic resonance image data set;

if none of said second magnetic resonance images analyzed by said processor shows arrival of said main bolus in said target area, providing a signal from said processor to said magnetic resonance data acquisition scanner that starts said diagnostic magnetic resonance image data acquisition protocol after said wait period, wherein said magnetic resonance data acquisition scanner is operated by the processor to acquire said diagnostic magnetic resonance image data set; and from said processor, making said diagnostic magnetic resonance image data set available in electronic form, as a data file.

2. A method as claimed in claim 1 comprising selecting an end of said monitoring interval so that a time period from said end of said monitoring interval until an end of said wait period is less than or equal to an acquisition time for an individual second magnetic resonance image in said plurality of second magnetic resonance images.

3. A method as claimed in claim 1 comprising providing a speech command after starting said diagnostic image data acquisition protocol, and calculating said wait period as said peak time minus a time until said speech command occurs.

4. A method as claimed in claim 1 comprising, in said processor, determining a temporal contrast agent progressive curve from said first magnetic resonance images, and using said temporal contrast agent progressive curve to identify said peak time.

5. A method as claimed in claim 1 comprising defining said second acquisition area to include an entrance-side edge at which said contrast agent enters said second acquisition area.

6. A method as claimed in claim 1 comprising defining said first acquisition area to be equal to or to include said target area.

7. A method as claimed in claim 1 comprising defining said second acquisition area in said processor dependent on image data of said first magnetic resonance images.

8. A method as claimed in claim 1 comprising operating said magnetic resonance data acquisition scanner to acquire said second magnetic resonance images with a magnetic resonance data acquisition sequence having an acquisition duration, for each of said second magnetic resonance images, of less than two seconds.

9. A method as claimed in claim 1 comprising operating said magnetic resonance data acquisition scanner to acquire said second magnetic resonance images with a magnetic resonance data acquisition sequence having an acquisition duration, for each of said second magnetic resonance images, of less than one second.

10. A method as claimed in claim 1 comprising operating said magnetic resonance data acquisition scanner to acquire said second magnetic resonance images with a magnetic resonance sequence wherein the length of the monitoring interval is selected so that at least five of said second magnetic resonance images are acquired in said monitoring interval.

11. A method as claimed in claim 1 comprising operating said magnetic resonance data acquisition scanner to acquire said second magnetic resonance images with a magnetic resonance sequence wherein the length of the monitoring interval is selected so that at least ten of said second magnetic resonance images are acquired in said monitoring interval.

12. A method as claimed in claim 1 comprising operating said magnetic resonance data acquisition scanner to acquire said second magnetic resonance images with a magnetic resonance sequence having an acquisition duration, for each of said second magnetic resonance images, of less than two seconds, and wherein the length of the monitoring interval is selected so that at least five of said second magnetic resonance images are acquired in said monitoring interval.

13. A method as claimed in claim 1 comprising operating said magnetic resonance data acquisition scanner to acquire said second magnetic resonance images with a magnetic resonance sequence having an acquisition duration, for each of said second magnetic resonance images, of less than one second, and wherein the length of the monitoring interval is selected so that at least ten of said second magnetic resonance images are acquired in said monitoring interval.

14. A magnetic resonance apparatus comprising:
a magnetic resonance data acquisition scanner, adapted to receive a patient therein;
a processor configured, after administering a test bolus of a contrast agent that includes less contrast agent than a subsequent main bolus to be administered to the patient to acquire a diagnostic magnetic resonance image data set, to operate said magnetic resonance data acquisition scanner to start and execute a magnetic resonance image data acquisition protocol in order to acquire first magnetic resonance images of a first acquisition area, which includes at least a portion of a target area of the patient to be acquired in said diagnostic magnetic resonance image data set;
said processor being provided with said first magnetic resonance images, and said processor being configured to automatically evaluate the first magnetic resonance images to determine a peak time of said test bolus in said target area, said peak time being a point in time of maximum concentration of said contrast agent in said target area;
a memory accessible by said processor, said memory being organized as k-space having a k-space center;
said processor, in a diagnostic magnetic resonance image data acquisition protocol, being configured to enter diagnostic magnetic resonance image data acquired from the patient into said k-space center at a time beginning after starting said diagnostic magnetic resonance image data acquisition protocol, and said processor being configured to calculate a wait period, which follows administration of said main bolus, as said peak time minus a duration until said entry of said diagnostic magnetic resonance image data into said k-space center begins after starting said magnetic resonance image data acquisition protocol;
said processor being configured to operate said magnetic resonance data acquisition scanner, after administering said main bolus to the patient, to acquire, in chronological succession, a plurality of second magnetic resonance images of a second acquisition area of the patient, which includes at least a portion of the target area, in a monitoring interval that is situated within said wait period;
said processor being successively provided with said second magnetic resonance images, and said processor, immediately upon individual acquisition thereof, being configured to successively analyze said second magnetic resonance images, as said second magnetic resonance images are supplied to said processor, to identify one of said second magnetic resonance images that shows arrival of said main bolus in said target area;
upon identifying said one of said second magnetic resonance images that shows arrival of said main bolus in said target area, said processor being configured to cause said magnetic resonance data acquisition scanner to terminate acquisition of said second magnetic resonance images and immediately start said diagnostic magnetic resonance image data acquisition protocol in which said processor operates said magnetic resonance data acquisition scanner to acquire said diagnostic magnetic resonance image data set;
if none of said second magnetic resonance images analyzed by said processor shows arrival of said main bolus in said target area, said processor being configured to cause said magnetic resonance data acquisition scanner to start said diagnostic magnetic resonance image data acquisition protocol after said wait period, in which said processor operates said magnetic resonance data acquisition scanner to acquire said diagnostic magnetic resonance image data set; and
said processor being configured to make said diagnostic magnetic resonance image data set available in electronic form, as a data file.

* * * * *